United States Patent [19]

Thyrum

[11] 4,004,453
[45] Jan. 25, 1977

[54] METHOD FOR DETECTING OIL IN WATER

[76] Inventor: Per T. Thyrum, 100-D Phelps Ave., New Brunswick, N.J. 08901

[22] Filed: Dec. 8, 1975

[21] Appl. No.: 638,471

[52] U.S. Cl. .......................... 73/61.1 R; 23/230 M; 23/253 TP
[51] Int. Cl.² ...................................... G01N 33/18
[58] Field of Search ............ 73/61.1 R; 23/230 HC, 23/230 M, 253 TP; 210/85

[56] References Cited

UNITED STATES PATENTS

| | | | |
|---|---|---|---|
| 1,925,254 | 9/1933 | John | 73/61.1 R X |
| 2,844,025 | 7/1958 | Joyce et al. | 73/61.1 R |
| 3,041,870 | 7/1962 | Levine | 73/61.1 R |
| 3,700,409 | 10/1972 | Zall | 23/230 HC X |

Primary Examiner—Richard C. Queisser
Assistant Examiner—Joseph W. Roskos
Attorney, Agent, or Firm—R. S. Sciascia; Henry Hansen

[57] ABSTRACT

Simple and economical methods for accurately determining low concentrations of particulate oil in water. In one method a sample of water is first filtered at a controlled rate. A dye-impregnated pad is pressed against the upstream surface of the filter element and then removed. The upstream surface of the filter element may now be observed with the eye against colorations of known concentrations for variations in color intensity clearly discernible within the range of 0 to 30 ppm (parts per million) by volume of oil-in-water. The dye-impregnated pad is prepared by submerging a white absorbent material in a saturated solution of an oil-soluble, water-insoluble dye, and drying them in a rack under vacuum. In another method, where the sample also contains discoloring pigmented contaminants, an intermediate pad is pressed between the filter element and the dye-impregnated pad, and its coloration compared to known standards. In lieu of the intermediate pad method, a thin prefilter is placed on the upstream surface of the filter element during filtering, then discarded, and the filter element is processed as described in the first method above.

27 Claims, 4 Drawing Figures

METHOD FOR DETECTING OIL IN WATER

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to methods for determining the presence in water of dispersed liquids of low solubility. More particularly, the invention relates to methods for quantitative analysis of very low concentrations of particulate oil in water.

Pollution control laws have led to an urgent need for a sensitive, rapid and simple method for measuring very low concentrations of oil in the water. For example, the Federal Water Pollution Control Act prohibits oil in waste water streams from ships within the off-shore 12 mile limit of the United States if such discharge causes a visible sheen upon the surface of the water. In the case of a Coast Guard Cutter, such a sheen is produced when the oil content of the water pumped overboard reaches between 20 and 30 ppm. At certain Naval installations, the maximum allowable oil and grease concentration in water discharges is only 5 ppm. Therefore, to be effective, a method for monitoring oil in waste water streams should be sensitive within a range of 0 to 30 ppm at 5 ppm minimum increments. Most currently available laboratory and automatic oil detection methods involve gravimetric or volumetric measurement after extracting the oil with volatile solvents or by centrifugal separation, or measurement of light absorption, scattering, or fluorescence. In general, such methods are not suitable for shipboard use because they are too time-consuming, expensive, insensitive, or require the services of a skilled analyst. Moreover, the accuracies of many of the prior art methods are greatly reduced by surfactants and solid contaminents often present in the bilge water of ships.

SUMMARY OF THE INVENTION

Accordingly, it is an object of the present invention to provide methods for quickly and quantitatively indicating low concentrations of particulate oil in water.

Another object of the invention is to provide quantitative analyses of particulate oil in water by inexpensive and simple methods which can be used in the field by unskilled technicians.

A further object of the invention is to provide oil detection methods which are not affected by the presence of surfactants in the water.

These and other objects and many of the attendant advantages of the invention will become more apparent from the detailed description hereinbelow.

Briefly, the invention comprises passing a specified volume of water sample through a filter element at a specified flow rate. Undissolved, particulate oil present in the water is retained by the matrix of the filter element. The concentration of oil on or near the upstream surface of the filter element is visualized by pressing this area against a surface which has been impregnated with an oil-indicating material. A visible stain is formed on the upstream surface of the filter element which is so noticeable that undissolved petroleum fuels and oils in concentrations within a range between 0 and 30 ppm by volume is easily detected. For samples containing solid as well as oily constituents, an intermediate pad or a prefilter may be used.

DESCRIPTION OF THE PREFERRED METHOD

Figure 1:
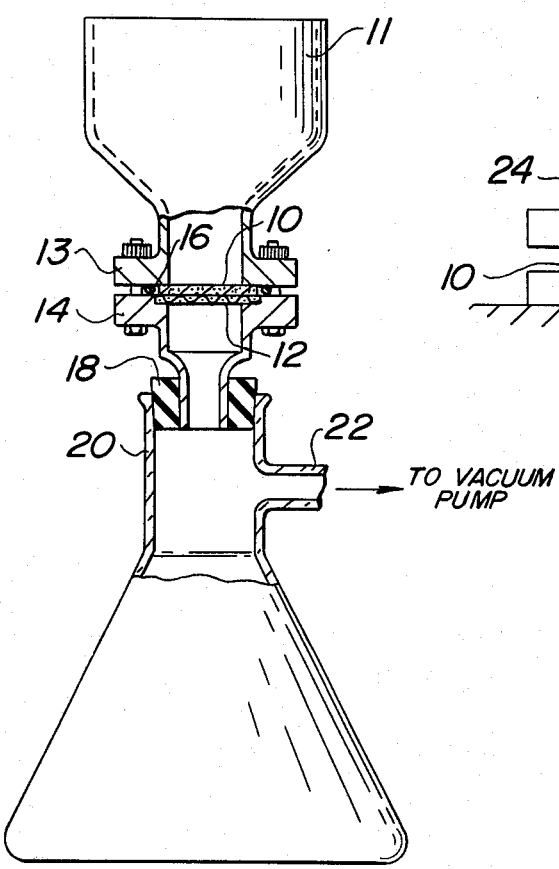
FIG. 1 schematically represents a vacuum-operated filter apparatus used according to the invention.

According to the invention, a sample of water is first filtered through an apparatus such as shown in FIG. 1. It is preferred that the sample containing oil types commonly present in ship bilges be pretreated with a small drop (about 10 ul) of 1% aqueous dispersion of surfactant, such as Span 85 by Atlas Chemical Industries. The sample is then agitated prior to filtering. The purpose of the surfactant is to aid in the uniform distribution of the suspended oil. The choice of surfactant should be guided by the suspected oil types. A filter element 10 in the apparatus is securely mounted on a support screen 12 by an annular locking flange 13, annular base flange 14, and a sealing gasket 16. Flange 10 communicates with a funnel 11 having a capacity for receiving a 500 ml sample of water. The lower end of the base flange 14 terminates in a reduced outlet within the neck portion of a flask 20 which includes a side opening 22 for connecting to a vacuum pump, not shown. An annular seal 18 between the outlet of base flange 14 and the neck portion of flask 20 maintains pressure integrity in the volume below element 10 and within flask 20. Apparatus for filtering the water may be of conventional design such as the Fluids Contamination Analysis Kit No. XX7104711 manufactured by the Millipore Corp.

A suitable element may consist of a white cellulose material such as unsized paper, paper pulp, and woven cotton cloth, glass fibers, or various polymeric materials such as nylon or polypropylene. In the example, a Millipore Absorbent Pad, Type AP10, of 1.85 inches diameter and 0.03 inch thick was used. This element is a white cellulose material resembling blotting paper and is generally used in the laboratory to support other filters, used in microbiological culturing, or to assist in drying other filters.

In the disclosed example, a 250 milliliter sample of water was poured into the funnel 11 and allowed to flow through the filter element 10. The filtration time for each sample was maintained between 30 and 50 seconds by application of a vacuum when gravity filtering was insufficient.

It is important that the flow rate during filtering be kept relatively constant for accurate results. In the disclosed example a flow rate between 300 and 400 milliliters per minute was used. In order to partially dry the filter element after filtration, air was then drawn through the system for 20 seconds using the vacuum at approximately 17 inches of mercury.

After filtration, the element 10 is removed and its upstream surface placed in contact with a dry pad 24 which has been impregnated with an oil-indicating dye. The pad 24 is preferably of the same material, size and thickness as the filtering element 10 but treated with an organic solution containing an oil-indicating material. The pad 24 may be dipped into the solution, or the solution may be applied to the pad such as by spraying or brushing so that the indicating material is uniformly spread over at least one side. The solvent is then removed by evaporation. It is important that the oil-indicating material be soluble in the types of oils to be detected, and be practically insoluble in water. The indicating material must either exhibit a color when viewed in white light or emit a visible fluorescence under ultraviolet light. In the disclosed example, the element containing the oil-indicating material was prepared by completely submerging the pads, identical to element 10, in an ethanol solution saturated with a blue, oil-soluble dye such as Oil Blue (E. I. DuPont deNemours and Company) or Automate Blue No. 8 (Morton Chemical Company). The pads are then dried under vacuum at 85° C.

Figure 2:
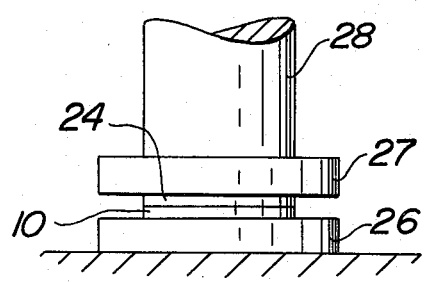
FIG. 2 schematically represents a hydraulic press used according to the invention.

Referring now to FIG. 2, the elements 10 and 24 are then placed between two steel plates 26 and 27 and clamped together under force by hydraulic press 28. The duration and force used should be constant in order to obtain accurate results, but the choice of pressure and time may be varied according to the nature of the material making up the matrices of the element 10 and pad 24. In the example, a force of 3000 lbs. and two minutes duration was found to be satisfactory.

Figure 3:
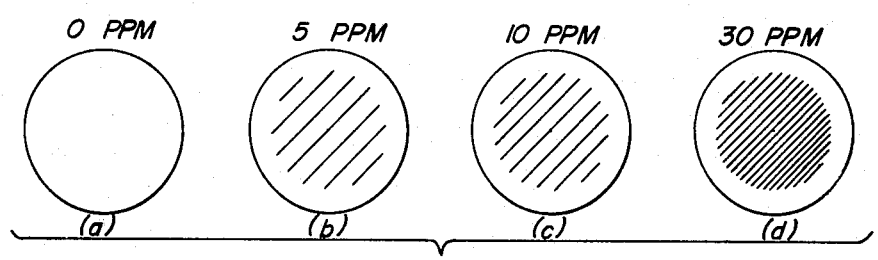
FIG. 3 represents filter elements of typical color intensity for corresponding increments of particulate oil concentrations in water samples.
Figure 4:
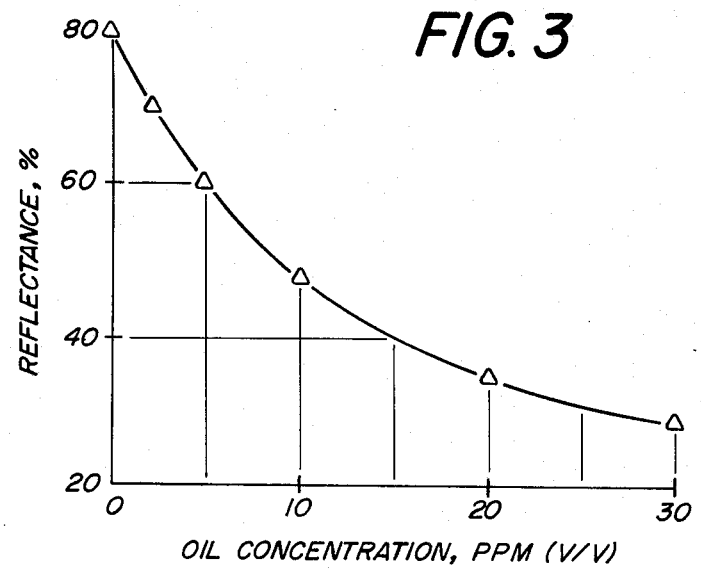
FIG. 4 is a graph of relative reflectance for increments of particulate oil concentrations in water samples.

After the compression step, the filter element 10 is removed and its upstream surface is inspected under white light for a color stain. In the disclosed example, incremental changes in concentrations of undissolved particulate oil dispersed in water produced clearly discernible corresponding shades of blue. Typical shades of blue for concentrations of zero, five, ten and 30 ppm are illustrated in FIG. 3. These elements could also be compared to a pre-calibrated "shade" chart for more accurate visible estimates.

Pure water samples or water containing surfactants will not lead to development in element 10 of any color change. However the presence of pigmented solid contaminants in the water sample analyzed may produce a stain in the filter element. This condition becomes clearly evident at the time of sample filtration. In such cases, a relatively thin intermediate pad of materials heretofore described may be interposed between element 10 and pad 24 and this combination compressed in the manner described. The intermediate pad is then removed and its surface, which was exposed to pad 24, is inspected under white light for the color stain. This stain represents undissolved particulate oils initially retained by element 10 and then transferred to the intermediate pad during compression. Alternative to using an intermediate pad, a thin prefilter may be used on the upstream surface of element 10. After the sample is filtered, the prefilter is discarded and the element 10 processed as described in the first method. A suitable prefilter was found to be a 2 micrometer pore size manufactured by Nuclepore Corporation. It consists of a polycarbonate membrane of uniform straight-through, cylindrical pores thereby holding on a small fraction of the oil contained in the sample, but filtering discoloring solid contaminants.

The pads or elements stained by the above processes may now be compared to a set of color intensity photographs of stain patterns produced by samples of known concentrations of the like oil.

It should now be apparent that the foregoing methods described provide a means for detecting very small quantities of undissolved particulate oil in water. It enables quantitative field testing for the detection of oil concentrations between 1 and 30 ppm by volume in water discharged from ships. The methods are readily adapted to the determination of oil pollutants in excess of 30 ppm by the use of sampling volumes smaller than that described in the preferred methods. The inventive methods provide a rapid, inexpensive and simple procedure which can be used by untrained personnel. They are not sensitive to dissolved oil and will work for any type of fuel or lubricating oil for which a soluble indicator dye can be found. It is not affected by the presence of common surfactants found in bilge water of ships.

It should be understood that various changes in the details, materials and arrangement of steps which have been hereindescribed and illustrated in order to explain the nature of the invention may be made by those skilled in the art within the principle and scope of the invention as described above.

What is claimed is:

1. A method for determining the presence of a first liquid of low solubility and low surface activity particulately dispersed in a second liquid, comprising:
    filtering a sample of said liquids through a porous filter element at a controlled flow rate;
    pressing a pad impregnated with an oil-soluble, water-insoluble dye against the upstream surface of the element; and
    removing said pad and observing the color stain on the surface of said element which was contiguous with said pad.

2. A method according to claim 1 wherein the process in preparing said dye-impregnated pad comprises the steps of: applying an organic solvent containing an oil-soluble, water insoluble dye to a pad; and removing said solvent by evaporation.

3. A method according to claim 2 wherein said pressing is at a preselected pressure.

4. A method according to claim 3 wherein said pressing is of a predetermined duration.

5. A method according to claim 4 wherein a method for preparing said sample of said mixture before filtering comprises: adding a surfactant; and agitating the sample.

6. A method according to claim 5 wherein said first and second liquids are oil and water, respectively.

7. A method according to claim 6 wherein said pressing is at a force of about 3000 pounds.

8. A method according to claim 7 wherein the duration of said pressing is about two minutes.

9. A method according to claim 8 wherein the sample is about 250 ml at a flow rate controlled to cause filtering between 30 and 50 seconds.

10. A method for determining the presence of a first liquid of low solubility and low surface activity particulately dispersed in a second liquid, comprising:
    filtering a sample of said liquids through a porous filter element having a prefilter on the upstream surface at a controlled flow rate, said prefilter having a polycarbonate membrane of uniform, straight-through cylindrical pores;
    removing said prefilter from said element;
    pressing a pad impregnated with an oil-soluble, water-insoluble dye against the upstream surface of the element; and removing said pad and observing the color stain on the surface of said element which was contiguous with said pad.

11. A method according to claim 10 wherein the process in preparing said dye-impregnated pad comprises the steps of:
applying an organic solvent containing an oil-soluble, water insoluble dye to a pad; and removing said solvent by evaporation.

12. A method according to claim 11 wherein said pressing is at a preselected pressure.

13. A method according to claim 12 wherein said pressing is of a predetermined duration.

14. A method according to claim 13 wherein a method for preparing the sample of said mixture before filtering comprises: adding a surfactant; and agitating the sample.

15. A method according to claim 14 wherein said first and second liquids are oil and water, respectively.

16. A method according to claim 15 wherein said pressing is at a force of about 3000 pounds.

17. A method according to claim 16 wherein the duration of said pressing is about two minutes.

18. A method according to claim 17 wherein the sample is about 250 ml at a flow rate controlled to cause filtering between 30 and 50 seconds.

19. A method for determining the presence of a first liquid of low solubility and low surface activity particulately dispersed in a second liquid, comprising:
filtering a sample of said liquids through a porous filter element at a controlled flow rate;
pressing a pad impregnated with an oil-soluble, water-insoluble dye interposed by a white intermediate pad against the upstream surface of the element; and
removing said intermediate pad and observing the color stain on the surface thereof which was contiguous with said dye-impregnated pad.

20. A method according to claim 19 wherein the process in preparing said dye-impregnated pad comprises the steps of:
applying an organic solvent containing an oil-soluble, water-insoluble dye to a pad; and removing said solvent by evaporation.

21. A method according to claim 20 wherein said pressing is at a preselected pressure.

22. A method according to claim 21 wherein said pressing is of a predetermined duration.

23. A method according to claim 22 wherein a method for preparing the sample of said mixture before filtering comprises:
adding a surfactant; and
agitating the sample.

24. A method according to claim 23 wherein said liquid mixture is water and oils.

25. A method according to claim 24 wherein said pressing is at a force of about 6000 pounds.

26. A method according to claim 25 wherein the duration of said pressing is about two minutes.

27. A method according to claim 26 wherein the sample is about 500 ml at a flow rate controlled to cause filtering between 60 and 100 seconds.

* * * * *